(12) United States Patent
Sanchez et al.

(10) Patent No.: US 6,839,612 B2
(45) Date of Patent: Jan. 4, 2005

(54) MICROWRIST SYSTEM FOR SURGICAL PROCEDURES

(75) Inventors: Dan Sanchez, Santa Barbara, CA (US); Darrin Uecker, Santa Barbara, CA (US); Oleg Svanidze, Santa Barbara, CA (US); James Wright, Santa Barbara, CA (US); Yulun Wang, Goleta, CA (US)

(73) Assignee: Institute Surgical, Inc., Sunnyvale, CA (US)

( * ) Notice: Subject to any disclaimer, the term of this patent is extended or adjusted under 35 U.S.C. 154(b) by 177 days.

(21) Appl. No.: 10/013,067

(22) Filed: Dec. 7, 2001

(65) Prior Publication Data

US 2003/0109957 A1 Jun. 12, 2003

Related U.S. Application Data

(63) Continuation of application No. PCT/US02/38787, filed on Dec. 4, 2002.

(51) Int. Cl.$^7$ .............................................. G06F 19/00
(52) U.S. Cl. ....................... 700/245; 700/251; 700/257; 700/262; 700/264; 700/258; 606/1; 606/130; 606/139; 606/102; 606/595; 318/568.11; 901/1
(58) Field of Search ................................ 700/245, 257, 700/262, 264, 258, 251, 246, 260, 261, 253; 414/1, 2; 606/130, 1, 102, 595, 139; 128/898; 901/2, 8, 15, 17, 29, 48, 1, 9, 46; 318/568.11, 568.12, 568.16, 568.17, 568.2; 180/8.1, 8.6

(56) References Cited

U.S. PATENT DOCUMENTS

| | | |
|---|---|---|
| 977,825 A | 12/1910 | Murphy |
| 3,171,549 A | 3/1965 | Orloff |
| 3,280,991 A | 10/1966 | Melton et al. |
| 3,923,166 A * | 12/1975 | Fletcher et al. ................. 414/4 |
| 4,058,001 A | 11/1977 | Waxman |
| 4,128,880 A | 12/1978 | Cray, Jr. |
| 4,221,997 A | 9/1980 | Flemming |
| 4,367,998 A | 1/1983 | Causer |
| 4,401,852 A | 8/1983 | Noso et al. |
| 4,456,961 A | 6/1984 | Price et al. |
| 4,460,302 A | 7/1984 | Moreau et al. |
| 4,474,174 A | 10/1984 | Petruzzi |
| 4,491,135 A | 1/1985 | Klein |
| 4,503,854 A | 3/1985 | Jako |
| 4,517,963 A | 5/1985 | Michel |
| 4,523,884 A | 6/1985 | Clement et al. |
| 4,586,398 A | 5/1986 | Yindra |
| 4,604,016 A | 8/1986 | Joyce |
| 4,616,637 A | 10/1986 | Caspari et al. |
| 4,624,011 A | 11/1986 | Watanabe et al. |

(List continued on next page.)

FOREIGN PATENT DOCUMENTS

| | | |
|---|---|---|
| DE | U 9204118.3 | 7/1992 |
| DE | 4310842 C2 | 1/1995 |
| EP | 0239409 A1 | 9/1987 |

(List continued on next page.)

OTHER PUBLICATIONS

Mack, Minimally invasive and robotic, 2001, Internet, pp. 568–572.*

(List continued on next page.)

Primary Examiner—Thomas G. Black
Assistant Examiner—McDieunel Marc
(74) Attorney, Agent, or Firm—Townsend & Townsend & Crew LLP; Mark D. Barrish, Esq.

(57) ABSTRACT

A medical robotic system with a handle assembly that is used to control a medical instrument. The handle assembly and medical instrument have five degrees of freedom. Five degrees of freedom may provide greater dexterity than medical robotic systems of the prior art with four or less degrees of freedom. Five degrees of freedom reduces the size and complexity of the instrument.

32 Claims, 5 Drawing Sheets

U.S. PATENT DOCUMENTS

| | | |
|---|---|---|
| 4,633,389 A | 12/1986 | Tanaka et al. |
| 4,635,292 A | 1/1987 | Mori et al. |
| 4,635,479 A | 1/1987 | Salisbury, Jr. et al. |
| 4,641,292 A | 2/1987 | Tunnell et al. |
| 4,655,257 A | 4/1987 | Iwashita |
| 4,672,963 A | 6/1987 | Barken |
| 4,676,243 A | 6/1987 | Clayman |
| 4,728,974 A | 3/1988 | Nio et al. |
| 4,762,455 A | 8/1988 | Coughlan et al. |
| 4,791,934 A | 12/1988 | Brunnett |
| 4,791,940 A | 12/1988 | Hirschfeld et al. |
| 4,794,912 A | 1/1989 | Lia |
| 4,815,006 A | 3/1989 | Andersson et al. |
| 4,815,450 A | 3/1989 | Patel |
| 4,837,734 A | 6/1989 | Ichikawa et al. |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,930,494 A | 6/1990 | Takehana et al. |
| 4,945,479 A | 7/1990 | Rusterholz et al. |
| 4,949,717 A | 8/1990 | Shaw |
| 4,954,952 A | 9/1990 | Ubhayakar et al. |
| 4,965,417 A | 10/1990 | Massie |
| 4,969,709 A | 11/1990 | Sogawa et al. |
| 4,969,890 A | 11/1990 | Sugita et al. |
| 4,979,933 A | 12/1990 | Runge |
| 4,979,949 A | 12/1990 | Matsen, III et al. |
| 4,980,626 A | 12/1990 | Hess et al. |
| 4,989,253 A | 1/1991 | Liang et al. |
| 4,996,975 A | 3/1991 | Nakamura |
| 5,019,968 A | 5/1991 | Wang et al. |
| 5,020,001 A | 5/1991 | Yamamoto et al. |
| 5,046,375 A | 9/1991 | Salisbury, Jr. et al. |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,105,367 A | 4/1992 | Tsuchihashi et al. |
| 5,109,499 A | 4/1992 | Inagami et al. |
| 5,123,095 A | 6/1992 | Papadopoulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,166,513 A | 11/1992 | Keenan et al. |
| 5,175,694 A | 12/1992 | Amato |
| 5,182,641 A | 1/1993 | Diner et al. |
| 5,184,601 A | 2/1993 | Putman |
| 5,187,574 A | 2/1993 | Kosemura et al. |
| 5,196,688 A | 3/1993 | Hesse et al. |
| 5,201,325 A | 4/1993 | McEwen et al. |
| 5,201,743 A | 4/1993 | Haber et al. |
| 5,217,003 A | 6/1993 | Wilk |
| 5,221,283 A | 6/1993 | Chang |
| 5,228,429 A | 7/1993 | Hatano |
| 5,230,623 A | 7/1993 | Guthrie et al. |
| 5,236,432 A | 8/1993 | Matsen, III et al. |
| 5,251,127 A | 10/1993 | Raab |
| 5,257,999 A | 11/1993 | Slanetz, Jr. |
| 5,271,384 A | 12/1993 | McEwen et al. |
| 5,279,309 A | 1/1994 | Taylor et al. |
| 5,282,806 A | 2/1994 | Haber |
| 5,289,273 A | 2/1994 | Lang |
| 5,289,365 A | 2/1994 | Caldwell et al. |
| 5,299,288 A | 3/1994 | Glassman et al. |
| 5,300,926 A | 4/1994 | Stoeckl |
| 5,303,148 A | 4/1994 | Mattson et al. |
| 5,304,185 A | 4/1994 | Taylor |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,408,409 A | 4/1995 | Glassman et al. |
| 5,410,638 A | 4/1995 | Colgate et al. |
| 5,417,210 A | 5/1995 | Funda et al. |
| 5,417,701 A | 5/1995 | Holmes |
| 5,422,521 A | 6/1995 | Neer et al. |
| 5,431,645 A | 7/1995 | Smith et al. |
| 5,434,457 A | 7/1995 | Josephs et al. |
| 5,442,728 A | 8/1995 | Kaufman et al. |
| 5,443,484 A | 8/1995 | Kirsch et al. |
| 5,445,166 A | 8/1995 | Taylor |
| 5,451,924 A | 9/1995 | Massimino et al. |
| 5,455,766 A | 10/1995 | Scheller et al. |
| 5,458,547 A | 10/1995 | Teraoka et al. |
| 5,458,574 A | 10/1995 | Machold et al. |
| 5,476,010 A | 12/1995 | Fleming et al. |
| 5,490,117 A | 2/1996 | Oda et al. |
| 5,490,843 A | 2/1996 | Hildwein et al. |
| 5,506,912 A | 4/1996 | Nagasaki et al. |
| 5,512,919 A | 4/1996 | Araki |
| 5,515,478 A | 5/1996 | Wang |
| 5,544,654 A | 8/1996 | Murphy et al. |
| 5,553,198 A | 9/1996 | Wang et al. |
| 5,562,503 A | 10/1996 | Ellman et al. |
| 5,571,110 A | 11/1996 | Matsen, III et al. |
| 5,572,999 A | 11/1996 | Funda et al. |
| 5,609,560 A | 3/1997 | Ichikawa et al. |
| 5,626,595 A | 5/1997 | Sklar et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |
| 5,695,500 A | 12/1997 | Taylor et al. |
| 5,696,574 A | 12/1997 | Schwaegerle |
| 5,696,837 A | 12/1997 | Green |
| 5,718,038 A | 2/1998 | Takiar et al. |
| 5,727,569 A | 3/1998 | Benetti et al. |
| 5,735,290 A | 4/1998 | Sterman et al. |
| 5,737,711 A | 4/1998 | Abe |
| 5,749,362 A | 5/1998 | Funda et al. |
| 5,754,741 A | 5/1998 | Wang et al. |
| 5,762,458 A | 6/1998 | Wang et al. |
| 5,766,126 A | 6/1998 | Anderson |
| 5,776,126 A | 7/1998 | Wilk et al. |
| 5,779,623 A | 7/1998 | Bonnell |

| | | | |
|---|---|---|---|
| 5,792,135 A | 8/1998 | Madhani et al. | |
| 5,792,178 A | 8/1998 | Welch et al. | |
| 5,797,900 A | 8/1998 | Madhani et al. | |
| 5,800,423 A | 9/1998 | Jensen | |
| 5,807,284 A | 9/1998 | Foxlin | |
| 5,807,377 A | 9/1998 | Madhani et al. | |
| 5,807,378 A | 9/1998 | Jensen et al. | |
| 5,808,665 A | 9/1998 | Green | |
| 5,810,880 A | 9/1998 | Jensen et al. | |
| 5,813,813 A | 9/1998 | Daum et al. | |
| 5,814,038 A | 9/1998 | Jensen et al. | |
| 5,817,084 A | 10/1998 | Jensen | |
| 5,825,982 A | 10/1998 | Wright et al. | |
| 5,827,319 A | 10/1998 | Carlson et al. | |
| 5,836,869 A | 11/1998 | Kudo et al. | |
| 5,844,824 A | 12/1998 | Newman et al. | |
| 5,855,583 A | 1/1999 | Wang et al. | |
| 5,859,934 A | 1/1999 | Green | |
| 5,860,995 A | 1/1999 | Berkelaar | |
| 5,876,325 A | 3/1999 | Mizuno et al. | |
| 5,878,193 A | 3/1999 | Wang et al. | |
| 5,882,206 A | 3/1999 | Gillio | |
| 5,887,121 A | 3/1999 | Funda et al. | |
| 5,898,599 A | 4/1999 | Massie et al. | |
| 5,904,702 A | 5/1999 | Ek et al. | |
| 5,906,630 A | 5/1999 | Anderhub et al. | |
| 5,911,036 A | 6/1999 | Wright et al. | |
| 5,920,395 A | 7/1999 | Schultz | |
| 5,931,832 A | 8/1999 | Jensen | |
| 5,950,629 A | 9/1999 | Taylor et al. | |
| 5,951,475 A | 9/1999 | Gueziec et al. | |
| 5,951,587 A | 9/1999 | Qureshi et al. | |
| 5,954,731 A | 9/1999 | Yoon | |
| 5,957,902 A | 9/1999 | Teves | |
| 5,971,976 A * | 10/1999 | Wang et al. | 606/1 |
| 5,980,782 A | 11/1999 | Hershkowitz et al. | |
| 5,984,932 A | 11/1999 | Yoon | |
| 6,001,108 A * | 12/1999 | Wang et al. | 606/130 |
| 6,024,695 A | 2/2000 | Taylor et al. | |
| 6,080,181 A | 6/2000 | Jensen et al. | |
| 6,106,511 A | 8/2000 | Jensen | |
| 6,120,433 A | 9/2000 | Mizuno et al. | |
| 6,132,368 A | 10/2000 | Cooper | |
| 6,201,984 B1 | 3/2001 | Funda et al. | |
| 6,206,903 B1 | 3/2001 | Ramans | |
| 6,223,100 B1 | 4/2001 | Green | |
| 6,226,566 B1 | 5/2001 | Funda et al. | |
| 6,231,526 B1 | 5/2001 | Taylor et al. | |
| 6,246,200 B1 | 6/2001 | Blumenkranz et al. | |
| 6,259,806 B1 | 7/2001 | Green et al. | |
| 6,309,397 B1 | 10/2001 | Julian et al. | |
| 6,312,435 B1 | 11/2001 | Wallace et al. | |
| 6,331,181 B1 | 12/2001 | Tierney et al. | |
| 6,346,072 B1 | 2/2002 | Cooper | |
| 6,364,888 B1 | 4/2002 | Nieneyer et al. | |
| 6,371,952 B1 | 4/2002 | Madhani et al. | |
| 6,419,429 B1 * | 7/2002 | Long et al. | 409/182 |
| 6,424,885 B1 * | 7/2002 | Niemeyer et al. | 700/245 |
| 6,580,969 B1 * | 6/2003 | Ishida et al. | 700/245 |
| 6,669,698 B1 * | 12/2003 | Tromanhauser et al. | 606/61 |
| 6,714,839 B2 | 3/2004 | Salisbury, Jr. et al. | |
| 2002/0165524 A1 * | 11/2002 | Sanchez et al. | 606/1 |
| 2003/0040758 A1 * | 2/2003 | Wang et al. | 600/130 |

FOREIGN PATENT DOCUMENTS

| | | |
|---|---|---|
| EP | 0424687 A1 | 5/1991 |
| EP | 0776738 A2 | 6/1997 |
| WO | WO 91/04711 | 4/1991 |
| WO | WO 92/20295 | 11/1992 |
| WO | WO 93/13916 | 7/1993 |
| WO | WO 94/18881 | 9/1994 |
| WO | WO 94/26167 | 11/1994 |
| WO | WO 97/15240 | 5/1997 |
| WO | WO 98/25666 | 6/1998 |

OTHER PUBLICATIONS

Oncology News, Surgeons in New York operate on patient in France, 2001, Internet, pp. 1–3.*

Mercury Bicycles, Mercury Olympic Onward Peter Pan Price, Sankey Stallard, 18888, Internet, pp. 1–5.*

Mack, Michael J., "Minimally Invasive and Robotic Surgery," *American Medical Association*, reprinted by JAMA, Feb. 7, 2001, vol. 285, No. 5, pp. 568–572.

http://www.intouchlive.com/journals/oncnews/n0112q.htm, "Surgeons in New York Operate on Patient in France," *Oncology News International*, vol. 10, No. 12 (Dec. 2001), 3 pages.

http://www.localhistory.scit.wlv.ac.uk/Museum/Transport/bicycles/Olympic.htm, "Mercury Bicycles," Mercury Olympic Onward Peter Pan Price Sankey Stallard, 1888, pp. 1–5.

"Endocorporeal Surgery Using Remote Manipulators" (Ned S. Rasor and J.W. Spickler) Remotely Manned Systems—Exploration and Operation in Space, California Institute of Technology 1973.

"A Survey Study of Teleoperators, Robotics, and Remote Systems Technology"(Arthur D. Alexander, III) Remotely Manned Systems—Exploration and Operation in Space California Institute of Technology 1973.

"Impacts of Telemation on Modem Society" (Arthur D. Alexander, III), On the Theory and Practice of Robots and Manipulators vol. II, 1974.

Transcript of a video presented by SRI at the 3rd World Congress of Endoscopic Surgery in Bordeaux on Jun. 18–20, 1992, in Washington on Apr. 9, 1992, and in San Diego, CA on Jun. 4–7, 1992 entitled "Telepresence Surgery—The Future of Minimally Invasive Medicine".

Statutory Declaration of Dr. Philip S. Green, presenter of the video entitled "Telepresence Surgery—The Future of Minimally Invasive Medicine".

Abstract of a presentation "Telepresence: Advanced Teleoperator Technology for Minimally Invasive Surgery" (P. Green et al.) given at the 3rd World Congress of Endoscopic Surgery in Bordeaux, Jun. 18–20, 1992.

Abstract of a presentation "Telepresence: Advanced Teleoperator Technology for Minimally Invasive Surgery", (P. Green et al.) given at "Medicine meets virtual reality" symposium in San Diego, Jun. 4–7, 1992.

Abstract of a presentation "Camera Control for Laparoscopic Surgery by Speech–Recognizing Robot: Constant Attention and Better Use of Personnel" (Colin Besant et al.) given at the 3rd World Congress of Endoscopic Surgery in Bordeaux, Jun. 18–20, 1992.

"A Literature Review: Robots in Medicine" (B. Preising et al.) IEEE Jun. 1991.

"Robots for the Operating Room" (Elizabeth Corcoran), The New York Times, Sunday Jul. 19, 1992, Section 3, p. 9, Column 1.

"Taming the Bull: Safety in a Precise Surgical Robot" (Russell H. Taylor et al.), IEEE 1991.

Abstract of a presentation "Design Considerations of a New Generation Endoscope Using Robotics and Computer Vision Technology" (S.M. Krishnan et al.) given at the 3rd World Congress of Endoscopic Surgery in Bordeaux, Jun. 18–20, 1992.

Abstract of a presentation "3–D Vision Technology Applied to Advanced Minimally Invasive Surgery Systems" given at the 3rd World Congress of Endoscopic Surgery in Bordeaux, Jun. 18–20, 1992.

"Analysis of the Surgeon's Grasp for Telerobotic Surgical Manipulation" (Frank Tendick and Lawrence Stark), IEEE 1989.

"Kinematic Control and Visual Display of Redundant Teleoperators" (Hardi Das et al.), IEEE 1989.

"A New System for Computer Assisted Neurosurgery" (S. Lavallee), IEEE 1989.

"An Advanced Control Micromanipulator for Surgical Applications" (Ben Gayed et al.), Systems Science vol. 13 1987.

"Force Feedback–Based Telemicromanipulator for Robot Surgery on Soft Tissues" (A.M. Sabatini et al.), IEEE 1989.

"Six–Axis Bilateral Control of an Articulated Slave Manipulator Using a Cartesian Master Manipulator" (Masao Inoue), Advanced Robotics 1990.

"On a Micro–Manipulator for Medical Application—Stability Consideration of its Bilateral Controller" (S. Majima et al.), Mechatronics 1991.

"Anthropomorphic Remote Manipulator", NASA Tech Briefs 1991.

"Controlling Remote Manipulators through Kinesthetic Coupling" (A.K. Bejczy), Computers in Mechanical Engineering 1983.

"Design of a Surgeon–Machine Interface for Teleoperated Microsurgery" (Steve Charles M.D. et al.), IEEE 1989.

"A Robot in an Operating Room: A Bull in a China Shop" (J.M. Dolan et al.), IEEE 1987.

Abstract of a presentation "Concept and Experimental Application of a Surgical Robotic System the Steerable MIS Instrument SMI" given at the 3rd World Congress of Endoscopic Surgery in Bordeaux, Jun. 18–20, 1992.

Abstract of a presentation given at the 3rd World Congress of Endoscopic Surgery in Bordeaux, Jun. 18–20, 1992, entitled "Session 15/1".

Abstract of a presentation "A Pneumatic Controlled Sewing Device for Endoscopic Application the MIS Sewing Instrument MSI" given at the 3rd World Congress of Endoscopic Surgery on Bordeaux, Jun. 18–20, 1992.

Abstract of a presentation given at the 3rd World Congress of Endoscopic Surgery in Bordeaux Jun. 18 to 20, 1992), entitled "Session 15/2".

Abstract of a presentation given at the 3rd World Congress of Endoscopic Surgery in Bordeaux (Jun. 18 to 20, 1992), entitled Session 15/4.

Abstract of a presentation given at the 3rd World Congress of Endoscopic Surgery in Bordeaux ( Jun. 18 to 20, 1992), entitled "Session 15/5".

"Properties of Master–Slave Robots" (C. Vibet), Motor–con 1987.

"A New Microsurgical Robot System for Corneal Transplantation" (Noriyuki Tejima), Precision Machinery 1988.

"Human/Robot Interaction via the Transfer of Power and Information Signals—Part I: Dynamics and Control Analysis" (H. Kazerooni), IEEE 1989.

"Human/Robot Interaction via the Transfer of Power and Information Signals—Part II: An Experimental Analysis"(H. Kazerooni), IEEE 1989.

"Power and Impedance Scaling in Bilateral Manipulation" (J. Edward Colgate), IEEE 1991.

"S.M.O.S.: Stereotaxial Microtelemanipulator for Ocular Surgery" (Aicha Guerrouad and Pierre Vidal), IEEE 1989.

"Motion Control for a Sheep Shearing Robot" (James P. Trevelyan et al.), Proceedings of the 1st International Symposium on Robotics Research, MIT, Cambridge, Massachusetts, USA, 1983.

"Robots and Telechirs" (M.W. Thring), Wiley 1983.

Industrial Robotics (Gordon M. Mair), Prentice Hall 1988 (pp. 41–43, 49–50, 54, 203–209 enclosed).

"Student Reference Manual for Electronic Instrumentation Laboratories" (Wolf et al.), Prentice Hall, New Jersey 1990, pp. 498 amd 499.

"Surgery in Cyberspace" (TAUBES), Discover magazine, Dec. 1994.

* cited by examiner

MICROWRIST SYSTEM FOR SURGICAL PROCEDURES

PCT/US02/38787, Dec. 4, 2002 is a CON Ser. No. 10/013,067 Dec. 3, 2001.

BACKGROUND OF THE INVENTION

1. Field of the Invention

The present invention relates to a handle assembly for a medical robotic system.

2. Background Information

Historically, surgery has been performed by making large incisions in a patient to provide access to the surgical site. There has been developed instruments that allow a surgeon to perform a procedure through small incisions in the patient. The instruments include an endoscope which has a camera that allows the surgeon to view the internal organs of the patient through a small incision. Such procedures are less traumatic to the patient and have shorter recovery times than conventional surgical procedures. Endoscopic instruments have even been used to perform minimally invasive heart surgery. Blockage of a coronary artery may deprive the heart of blood and oxygen required to sustain life. The blockage may be removed with medication or by an angioplasty. For severe blockage, a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery is then severed and attached to the artery at the point of incision. The internal mammary artery bypasses the blocked area of the artery to again provide a full flow of blood to the heart. Splitting the sternum and opening the chest cavity can create a tremendous trauma to the patient. Additionally, the cracked sternum prolongs the recovery period of the patient.

Computer Motion of Goleta, Calif. provides a system under the trademark ZEUS that allows a surgeon to perform a minimally invasive surgery, including CABG procedures. The procedure is performed with instruments that are inserted through small incisions in the patient's chest. The instruments are controlled by robotic arms. Movement of the robotic arms and actuation of instrument end effectors are controlled by the surgeon through a pair of handles and a foot pedal that are coupled to an electronic controller. Alternatively, the surgeon can control the movement of an endoscope used to view the internal organs of the patient through voice commands.

The incisions create pivot points for the medical instruments. The pivot points constrain movement of the instruments within the patient to four degrees of freedom; translation, pan, tilt and rotation of the instrument shaft. Additionally, the pivot point may cause a reverse movement of the instrument. For example, leftward movement of the system input handle may actually cause a rightward movement of the instrument. The surgeon must compensate for such constraints, thereby increasing the difficulty of using the system for performing a medical procedure.

It would be desirable to provide a robotic handle that gives the user the sensation of controlling the tip of the instrument. It would also be desirable to generally improve the ergonomics of medical robotic master handles.

There have been developed medical robotic systems that create six degrees of freedom for the surgical instruments. Six degrees of freedom requires relatively complex mechanism that increases the size and cost of the system. It would be desirable to provide an effective medical robotic system that would only require five degrees of freedom.

BRIEF SUMMARY OF THE INVENTION

A master robotic handle assembly that has only five degrees of freedom. The master handle assembly is used to move a robotically controlled surgical instrument.

DETAILED DESCRIPTION

Disclosed is a medical robotic system with a handle assembly that is used to control a medical instrument. The handle assembly and medical instrument have five degrees of freedom. Five degrees of freedom may provide greater dexterity than medical robotic systems of the prior art with four or less degrees of freedom. Five degrees of freedom reduces the size and complexity of the instrument and the overall robotic system.

Figure 1:
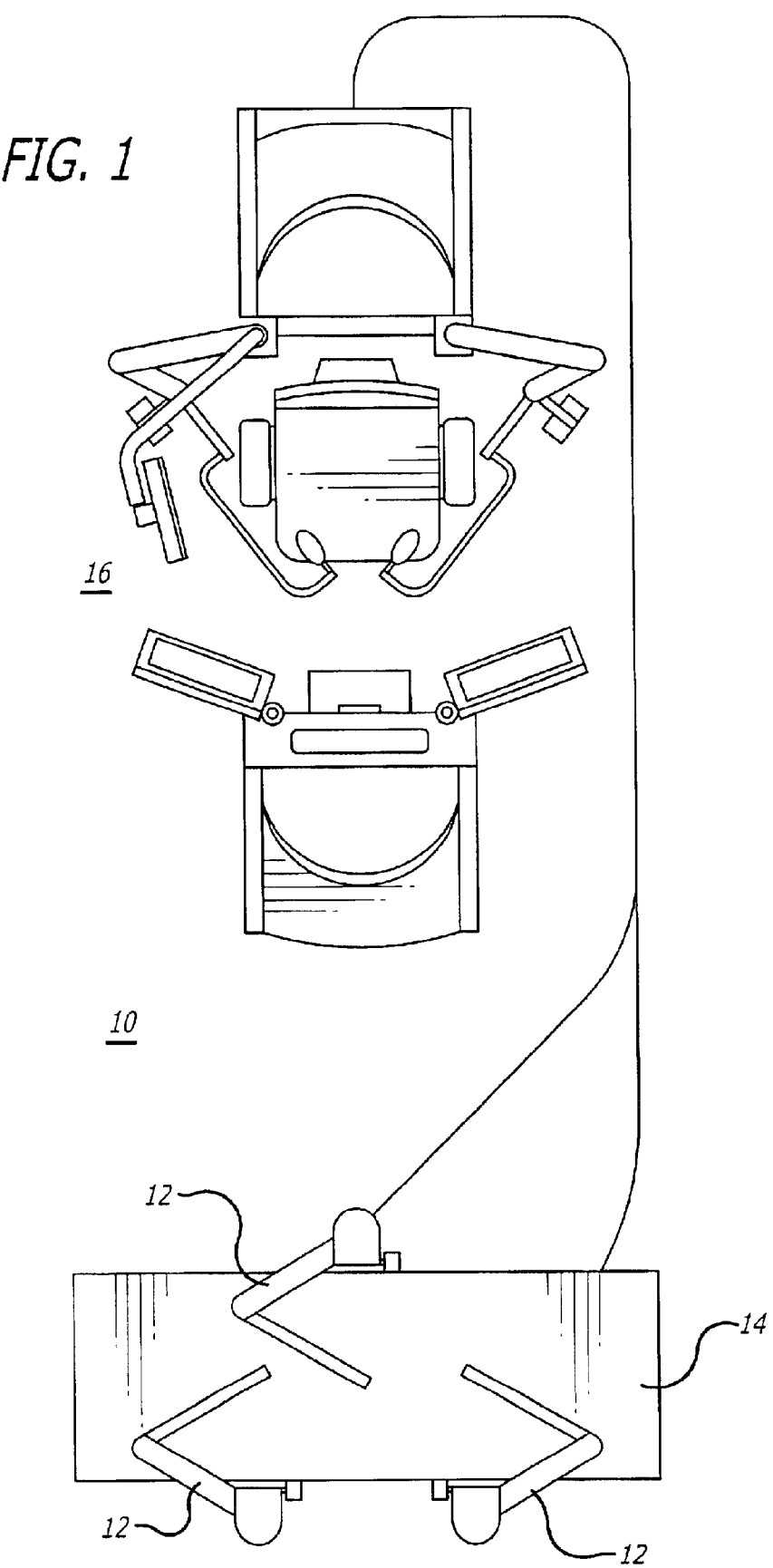
FIG. 1 is a top view of an illustration of a robotic system.

Referring to the drawings more particularly by reference numbers, FIG. 1 shows a robotic system 10. The system 10 may include a plurality of robotic arms 12 located adjacent to a table 14. Two of the robotic arms 12 may control the movement of corresponding medical instruments (not shown). The third robotic arm 12 may control the movement of an endoscope (not shown). The robotically controlled instruments and endoscope may be used to perform a minimally invasive medical procedure on a patient lying on the table 14.

The robotic arms 12 and accompanying instruments may be the same or similar to robotic products sold by Computer Motion under the trademarks AESOP and ZEUS. Although three robotic arms 12 are shown and described, it is to be understood that the system 10 may have a different number of arms 12.

The robotic arms 12 are controlled from a "surgeon" area 16. The surgeon area 16 may be located adjacent to the table 14. Alternatively, the surgeon area 16 may be coupled to the robotic arms 12 through a telecommunications link to allow a surgeon to have remote input into the system 10.

Figure 2:
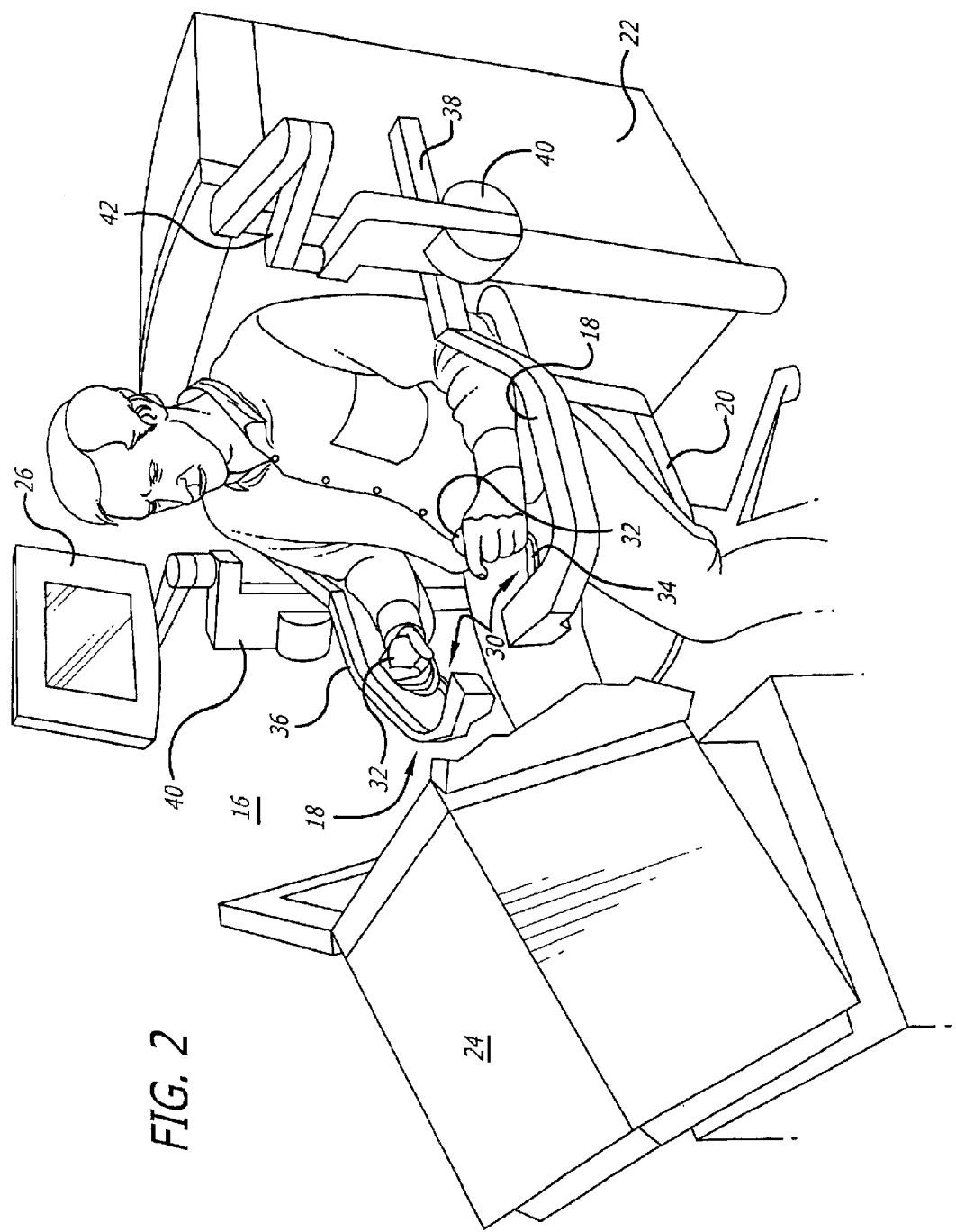
FIG. 2 is a perspective view of a surgeon control area of the robotic system.

FIG. 2 shows a surgeon area 16. The surgeon area 16 includes a pair of handle assemblies 18 located adjacent to a surgeons chair 20. The handle assemblies 18 are coupled to a controller 22 that is also coupled to the robotic arms 12 and medical instruments. The controller 22 may include one or more microprocessors, memory devices, drivers, etc. that convert input information from the handle assemblies 18 into output control signals which move the robotic arms and/or actuate the medical instruments.

The surgeon's chair 20 and handle assemblies 18 may be in front of a video console 24. The video console 24 may be linked to the endoscope to provide video images of the patient. The surgeon's area 16 may also include a computer screen 26 coupled to the controller 22. The screen 26 may display graphical user interfaces (GUIs) that allow the surgeon to control various functions and parameters of the system 10.

Each handle assembly 18 may include a handle/wrist assembly 30. The handle/wrist assembly 30 has a handle 32 that is coupled to a wrist 34. The wrist 34 is connected to a forearm linkage 36 that slides along a slide bar 38. The slide bar 38 is pivotally connected to an elbow joint 40. The elbow joint 40 is pivotally connected to a shoulder joint 42 that is attached to the controller 22.

Figure 3:
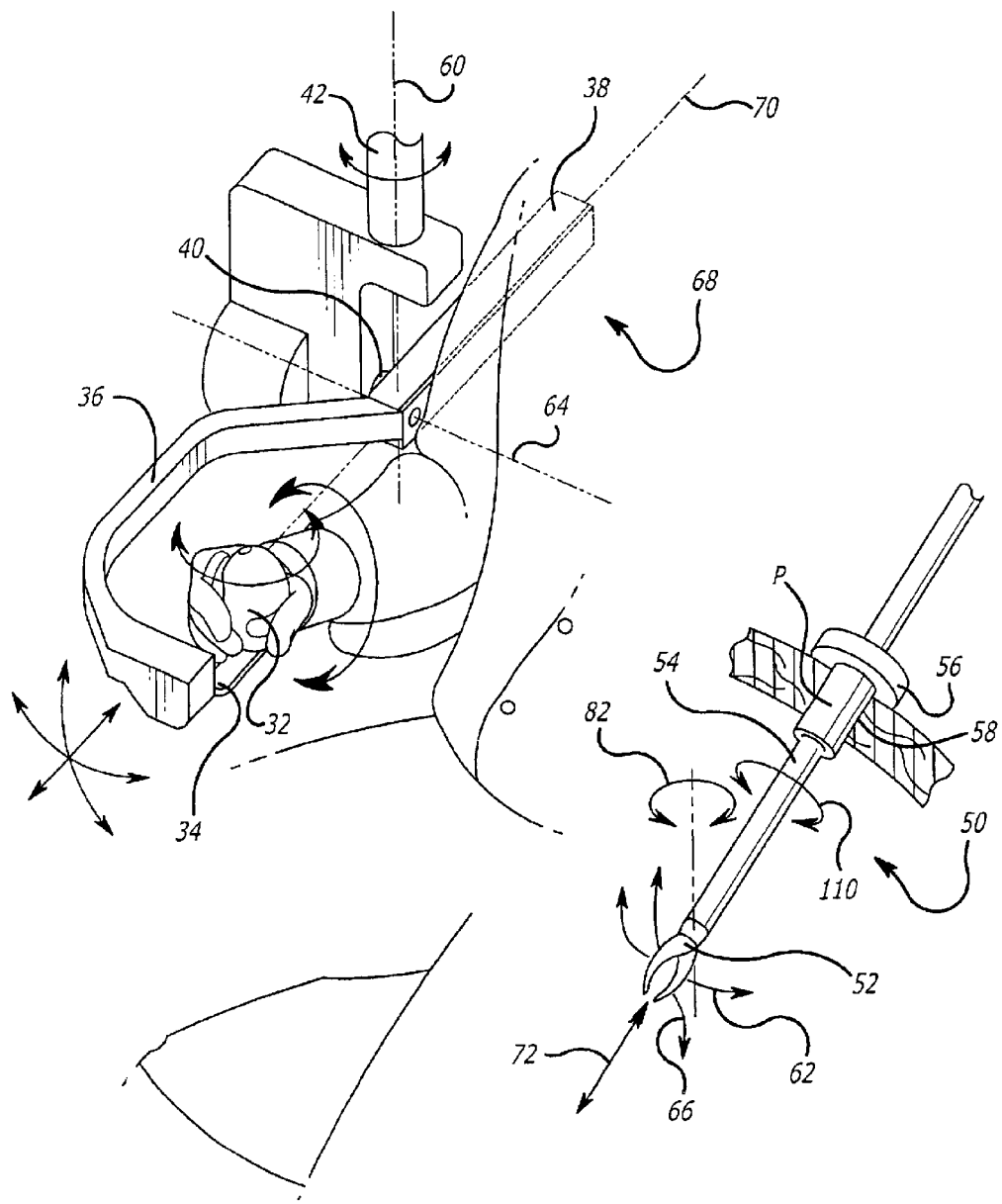
FIG. 3 is a perspective view of a handle assembly of the robotic system used to control a medical instrument.

FIG. 3 shows a handle assembly 18 superimposed with a medical instrument 50. The instrument 50 includes an end effector 52 attached to an instrument shaft 54. The shaft 54 extends through a cannula 56 inserted through an incision of a patient 58. The incision defines a pivot point P for the medical instrument 50.

The shoulder joint 42 includes a sensor (not shown) that provides feedback on the movement of the handle about a shoulder axis 60. The sensor may be a mechanical encoder, optical encoder, etc. or other device which provides an output signal that corresponds to a position of the handle 32 about the shoulder axis 60. The output of the shoulder sensor is provided to the controller 22. The controller 22 performs a series of computations to determine a corresponding movement of the medical instrument 50. The computations may include one or more transformation and kinematic equations. The controller 22 provides output signals to the corresponding robotic arm 12 to move the instrument 50 about point P as indicated by the arrow 62.

The elbow joint 40 includes a sensor (not shown) that provides positional feedback on the position of the assembly about an elbow axis 64. The controller 22 utilizes the positional feedback to drive the robotic arm and move the instrument in the direction indicated by the arrow 66.

The forearm linkage 36 and slide bar 38 create a translator 68 that allows linear movement of the linkage 36 along a translator axis 70. The translator axis 70 intersects with the axes 60 and 64. The translator 68 has a sensor (not shown) that provides feedback information that is used to drive the robotic arm and move the instrument 50 in the direction indicated by the arrows 72.

When transforming movement of the handle 32 to movement of the instrument 50 the controller 22 may equate the intersection of the axes 60, 64 and 70 to the instrument pivot point P. Equating the intersection of the axis 60, 64 and 70 with the pivot point P provides a kinematic relationship such that the surgeon "feel" like they are actually moving the instrument 50. Additionally, the length of the forearm linkage and location of the handle are such that the surgeon is provided with the sensation that they are holding and moving the distal end of the instrument. These relationships also improve the ergonomics of the handle assembly and the ease of use of the robotic system as a whole. The transformation and kinematic equations may be similar to the equations used in the AESOP and ZEUS products with the signs (+/−) reversed to account for the elbow axis 64 being behind the surgeon.

The handle assembly 18 has only five degrees of freedom; handle spin, wrist, translator, elbow and shoulder. Having only five degrees of freedom reduces the complexity of the system 10. The medical instrument 50 thus only needs a wrist with one degree of freedom which reduces the complexity, size and corresponding cost of the instrument. The configuration of the handle assembly allows the surgeon to perform any movement of the instrument with only five degrees of freedom.

Figure 4:
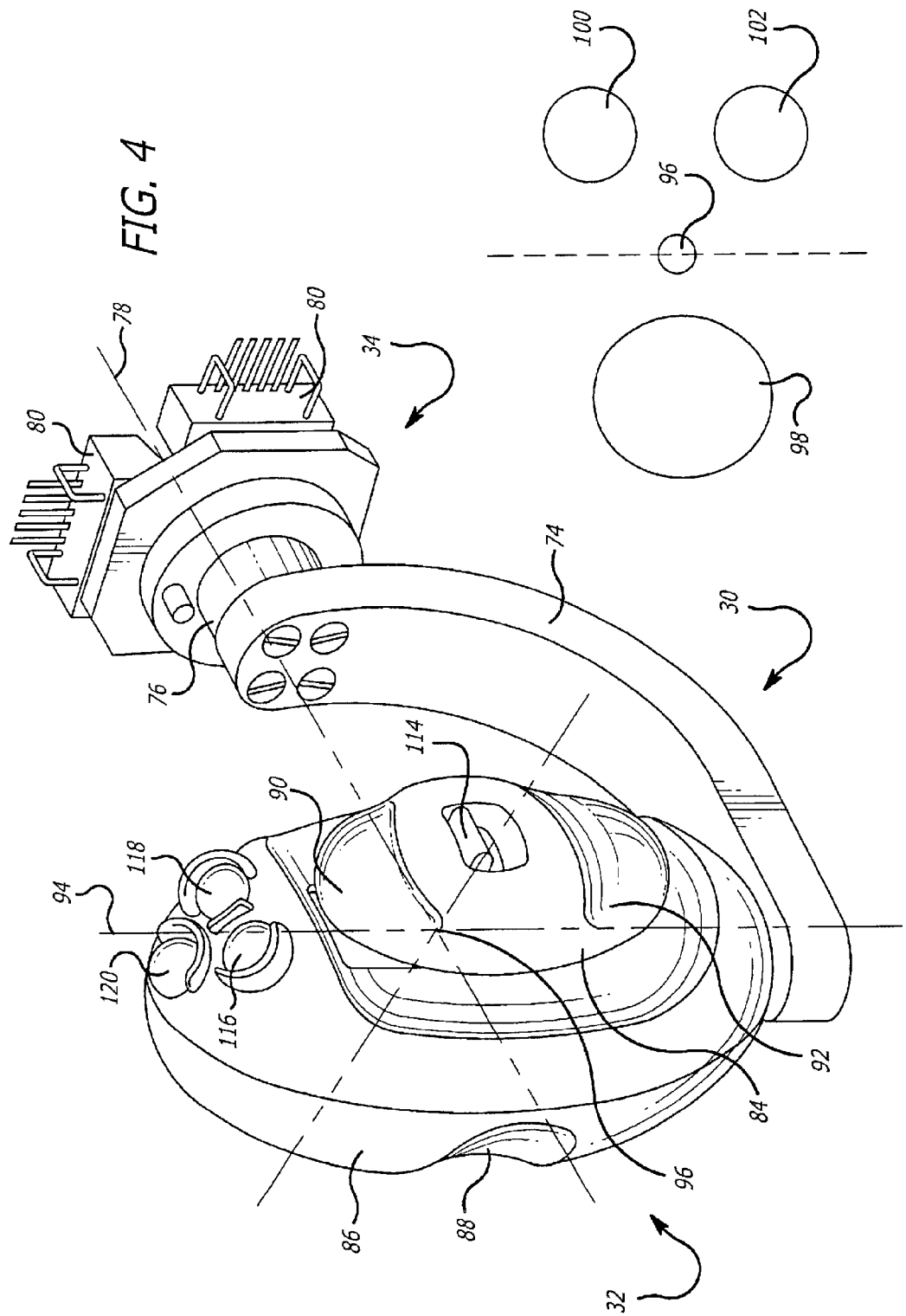
FIG. 4 is an enlarged perspective view of a wrist assembly of the robotic system controlled by a user's hand.
Figure 5:
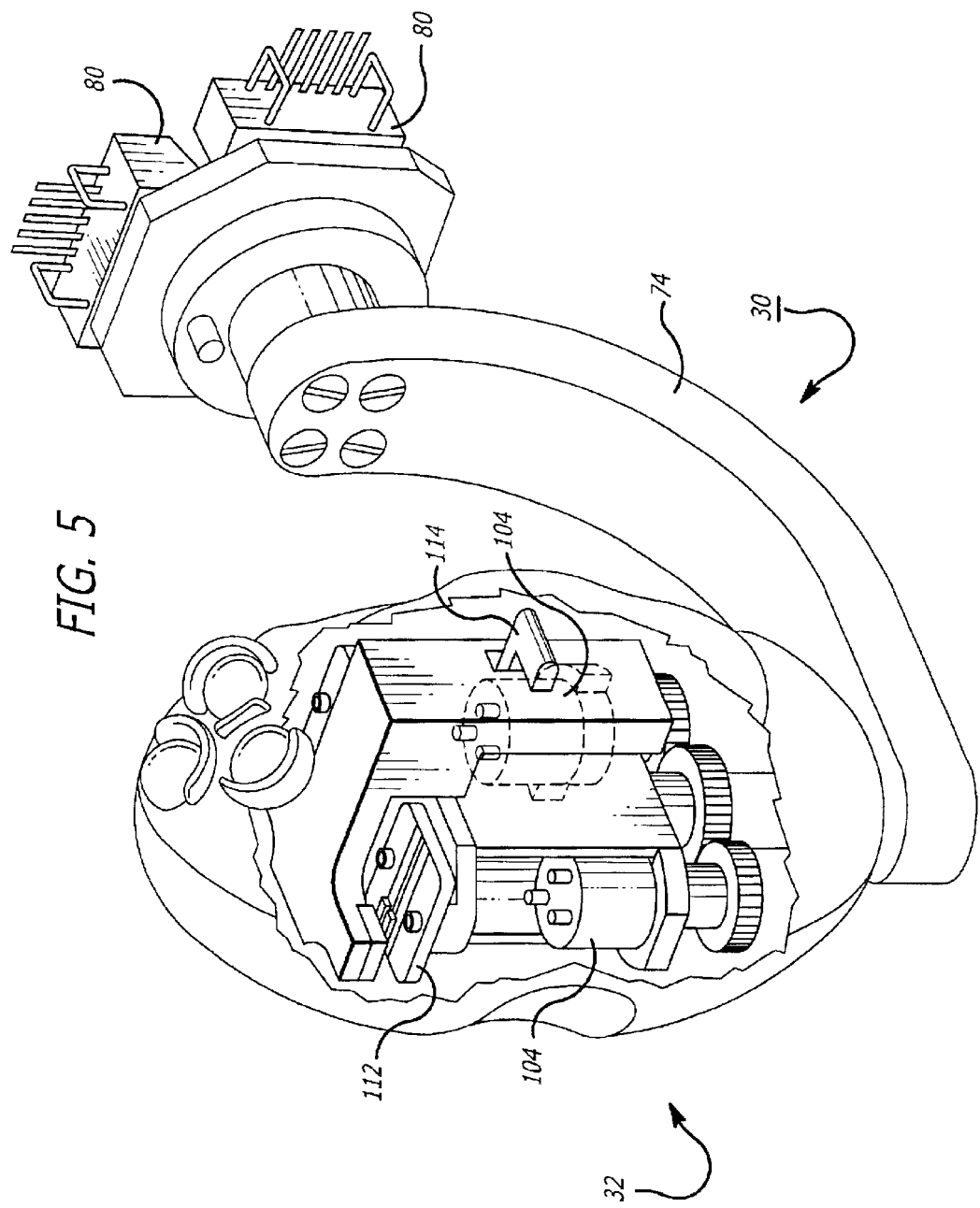
FIG. 5 is a sectional perspective view of the handle/wrist assembly.

FIGS. 4 and 5 show the wrist/handle assembly 30. The wrist 34 includes a joint shaft 74 that is coupled to the forearm linkage 36 by a roll bearing 76. The roll bearing 76 allows the handle 32 to rotate about a roll axis 78. The roll axis 32 may further include a sensor 80 that provide positional feedback to the controller 22. Movement of the handle 32 about the roll axis 78 may cause a corresponding rotation of the instrument end effector 52 in the direction indicated by the arrows 110 in FIG. 3.

The handle 32 includes a grasper 84 that is coupled to a handle housing 86. The housing 86 and grasper 84 are preferably shaped as an ellipsoid that allows the user to more easily grasps the handle 32 with their hand. The housing 86 may have a thumb groove 88 that receives the user's thumb. The grasper 84 may have a pair of grooves 90 and 92 to receive the index and middle fingers of the user, respectively.

The handle 32 can rotate about a wrist axis 94. The wrist 32 provides a fifth degree of freedom not found in medical robotic systems of the prior art. The wrist 32 may include a sensor 104 that provides positional feedback for the controller 22. To improve the ergonomics of the wrist/handle assembly 30 the wrist axis 94 preferably intersects the roll axis 78 at a centroid 96 located between the thumb 98, index finger 100 and middle finger 102 of the user's hand. It has been found that such a configuration creates a more ergonomically correct feel of the handle 32 and movement of the handle assembly 30.

The sensors 104 provide positional feedback information to the controller 22 which is used to spin the medical instrument 50 as indicated by the arrows 82 in FIG. 3.

The grasper 84 can be depressed by user. The grasper 84 is coupled to a sensor 112 which provides feedback information to the controller 22. The feedback information is used by the controller 22 to actuate the end effector 52 shown in FIG. 3. By way of example, depressing the grasper 84 may close the end effector 52. The grasper 84 may include a switch 114 that allows the user to lock the position of the grasper 84 and the end effector 52 of the corresponding medical instrument. The locking switch 114 may be coupled to a ratchet (not shown) that allows the grasper 84 and corresponding end effector 52 to be locked at a number of different positions.

The handle 32 may have a plurality of buttons 116, 118 and 120 that can be depressed by the user. By way of example, button 116 may be used to activate a cutting mode on a cauterizing end effector. Button 118 may be used to activate a coagulating medical instrument. The button 120 may be used to used to vary different functions of the system.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A robotic master handle assembly that has only five degrees of freedom, comprising:

a spinning handle; a wrist joint coupled to said handle;

a translator that is coupled to said wrist joint;

an elbow joint coupled to said translator; and a shoulder joint coupled to said elbow joint, wherein said handle is manipulated by a user's hand that has a centroid located between a thumb, an index finger and a middle finger, and said wrist joint allows said handle to rotate about a wrist axis that intersects the roll axis at the centroid of the user's hand.

2. The assembly of claim 1, wherein said handle includes a grasper that is coupled to a handle housing, said grasper includes a pair of grooves and said handle housing includes a groove.

3. The assembly of claim 2, wherein said grasper includes a switch.

4. The assembly of claim 2, wherein said handle housing includes a plurality of buttons.

5. A robotic master handle assembly that has only five degrees of freedom, comprising:

handle means for being rotated about a roll axis;

wrist means for allowing rotation of said handle means about a wrist axis;

translator means for allowing translation of said wrist means and said handle means;

elbow means for allowing rotation of said translator means, said wrist means and said handle means about an elbow axis; and shoulder means for allowing rotation of said elbow means, said translator means, said wrist means and said handle means about a shoulder axis, wherein said handle means is manipulated by a user's hand that has a centroid located between a thumb, an index finger and a middle finger, and the wrist axis intersects the roll axis at the centroid of the user's hand.

6. The assembly of claim 5, wherein said handle means includes a grasper that is coupled to a handle housing, said grasper includes a pair of grooves and said handle housing includes a groove.

7. The assembly of claim 6, wherein said grasper includes a switch.

8. The assembly of claim 6, wherein said handle housing includes a plurality of buttons.

9. A robotic system with a master handle assembly that has only five degrees of freedom, comprising:

a robotic arm;

a medical instrument coupled to said robotic arm;

a controller coupled to said robotic arm and said medical instrument;

a spinning handle coupled to said controller; a wrist joint that is coupled to said handle;

a translator that is coupled to said wrist joint; an elbow joint coupled to said translator; and a shoulder joint coupled to said wrist joint, wherein said handle is manipulated by a user's hand that has a centroid located between a thumb, an index finger and a middle finger, said wrist allows the handle to be rotated about a wrist axis that intersects the roll axis at the centroid of the user's hand.

10. The system of claim 9, wherein said handle includes a grasper that coupled to a handle housing, said grasper includes a pair of grooves and said handle housing includes a groove.

11. The system of claim 10, wherein said grasper includes a switch.

12. The system of claim 10, wherein said handle housing includes a plurality of buttons.

13. A robotic system, comprising:

a medical instrument;

robotic means for moving said medical instrument;

handle means for being rotated about a roll axis to spin the medical instrument;

wrist means for allowing rotation of said handle means about a wrist axis to move said medical instrument;

translator means for allowing translation of said wrist means and said handle means to translate said medical instrument;

elbow means for allowing rotation of said translator means, said wrist means and said handle means, to move said medical instrument; and shoulder means for allowing rotation of said elbow means, said translator means, said wrist means and said handle means, to move said medical instrument, wherein said handle means is manipulated by a user's hand that has a centroid located between a thumb, an index finger and a middle finger, said wrist allows said handle to rotate about a wrist axis that intersects the roll axis at the centroid of the user's hand.

14. The system of claim 13, wherein said handle means includes a grasper that is coupled to a handle housing, said grasper includes a pair of grooves and said handle housing includes a groove.

15. The system of claim 14, wherein said grasper includes a switch.

16. The system of claim 14, wherein said handle housing includes a plurality of buttons.

17. A method for operating a master handle assembly that has only five degrees of freedom, comprising:

rotating a handle about a roll axis;

rotating the handle about a wrist axis;

translating the handle relative to a translation axis;

rotating the handle about an elbow axis;

rotating the handle about a shoulder axis; and manipulating said handle means with a user's hand that has a centroid located between a thumb, an index finger and a middle finger, said wrist allows said handle to rotate about a wrist axis that intersects the roll axis at the centroid of the user's hand.

18. The method of claim 17, wherein rotating the handle spins a medical instrument.

19. The method of claim 17, wherein rotating the handle about the wrist axis moves a medical instrument.

20. The method of claim 17, wherein moving the wrist and handle along the translation axis moves a medical instrument.

21. A robotic system, comprising:

a robotic arm;

a medical instrument coupled to said robotic arm, said medical instrument pivots about a pivot point located at an incision of a patient;

a handle;

a translator coupled to said handle, said translator allows movement of said handle relative to a translator axis;

an elbow coupled to said translator, to allow movement of said handle about an elbow axis that intersects with the translator axis;

a shoulder coupled to said elbow to allow movement of said handle about a shoulder axis that intersects the elbow axis and the translator axis;

a controller coupled to said robotic arm, said translator, said elbow and said shoulder to control movement of said surgical instrument such that the intersection of the translator, elbow and shoulder axis corresponds to the pivot point; and a wrist that allows said handle to be rotated about a wrist axis, said handle spins about a roll axis, wherein said handle is manipulated by a user's hand that has a centroid located between a thumb, an index finger and a middle finger, and the wrist axis intersects the roll axis at the centroid of the user's hand.

22. The system of claim 21, wherein said handle includes a grasper that is coupled to a handle housing, said grasper includes a pair of grooves and said handle housing includes a groove.

23. The system of claim 22, wherein said grasper includes a switch.

24. The system of claim 21, wherein said handle housing includes a plurality of buttons.

25. A robotic system, comprising:
   a medical instrument that pivots about a pivot point located at an incision of a patient;
   robotic means for moving said medical instrument;
   handle means for being rotated about a roll axis to spin said medical instrument;
   translator means for allowing movement of said handle means relative to a translator axis;
   elbow means for allowing rotation of said handle means about an elbow axis that intersects the translator axis;
   shoulder means for allowing rotation of said handle means about a shoulder axis that intersects the translator axis;
   controller means for moving said robotic means in response to movement of said handle means wherein the intersection of the translation, elbow and shoulder axis corresponds to the pivot point; and
   wrist means for allowing said handle means to be rotated about a wrist axis, said handle means spins about a roll axis, wherein said handle means is manipulated by a user's hand that has a centroid located between a thumb, an index finger and a middle finger, and the wrist axis intersects with the roll axis at the centroid of the user's hand.

26. The system of claim 25, wherein said handle means includes a grasper that is coupled to a handle housing, said grasper includes a pair of grooves and said handle housing includes a groove.

27. The system of claim 25, wherein said grasper includes a switch.

28. The system of claim 25, wherein said handle housing includes a plurality of buttons.

29. A master robotic handle assembly that has only five degrees of freedom, comprising:
   a handle;
   a first joint that provides a first degree of freedom for said handle;
   a second joint that provides a second degree of freedom for said handle;
   a third joint that provides a third degree of freedom for said handle;
   a fourth joint that provides a fourth degree of freedom for said handle; and
   a fifth joint that provides a fifth degree of freedom for said handle.

30. A master robotic handle assembly that has only five degrees of freedom, comprising:
   a handle;
   first means for providing said handle with a first degree of freedom;
   second means for providing said handle with a second degree of freedom;
   third means for providing said handle with a third degree of freedom;
   fourth means for providing said handle with a fourth degree of freedom; and
   fifth means for providing said handle with a fifth degree of freedom.

31. A robotic system that has only five degrees of freedom, comprising:
   a robotic arm;
   a medical instrument which has an end effector that can move in a first direction, a second direction, a third direction, a fourth direction and a fifth direction; and
   a handle that has a first degree of freedom that corresponds to movement of said end effector in the first direction, a second degree of freedom that corresponds to movement of said end effector in the second direction, a third degree of freedom that correspond to movement of said end effector in the third direction, a fourth degree of freedom that corresponds to movement of said end effector in the fourth direction, and a fifth degree of freedom that corresponds to movement of said end effector in the fifth direction.

32. A method for operating a robotic system that has only five degrees of freedom, comprising:
   moving a handle about a first degree of freedom to move an end effector of a medical instrument in a first direction;
   moving the handle about a second degree of freedom to move the end effector in a second direction;
   moving the handle about a third degree of freedom to move the end effector in a third direction;
   moving the handle about a fourth degree of freedom to move the end effector in a fourth direction; and
   moving the handle about a fifth degree of freedom to move the end effector in a fifth direction.

* * * * *

UNITED STATES PATENT AND TRADEMARK OFFICE
CERTIFICATE OF CORRECTION

PATENT NO. : 6,839,612 B2
DATED : January 4, 2005
INVENTOR(S) : Dan Sanchez

It is certified that error appears in the above-identified patent and that said Letters Patent is hereby corrected as shown below:

Title page,
Item [73], Assignee, delete info and add the following:
-- Intuitive Surgical, Inc. Sunnyvale, CA --.

Signed and Sealed this

Eleventh Day of October, 2005

JON W. DUDAS
*Director of the United States Patent and Trademark Office*